United States Patent [19]

Tsukihara

[11] Patent Number: 5,715,328
[45] Date of Patent: Feb. 3, 1998

[54] METHOD AND APPARATUS FOR DIAGNOSING WALL OF COKING CHAMBER OF COKE BATTERY

[75] Inventor: Yuji Tsukihara, Kurashiki, Japan

[73] Assignee: Kawasaki Steel Techno-Research Corporation, Hyogo, Japan

[21] Appl. No.: 600,048

[22] Filed: Feb. 12, 1996

[30] Foreign Application Priority Data

Feb. 17, 1995 [JP] Japan .................. 7-029233

[51] Int. Cl.⁶ .................. G06T 5/40
[52] U.S. Cl. .................. 382/141; 382/171; 348/83
[58] Field of Search .................. 382/108, 141, 382/171, 172, 173, 100; 348/82, 83, 86, 128; 110/349, 338, 230, 193; 29/402.18; 202/227, 248, 215; 266/281; 374/149, 4

[56] References Cited

U.S. PATENT DOCUMENTS

| | | | |
|---|---|---|---|
| 4,131,914 | 12/1978 | Bricmont | 348/83 |
| 4,577,385 | 3/1986 | Omae et al. | 29/402.18 |
| 4,907,281 | 3/1990 | Hirvonen et al. | 382/100 |
| 5,425,279 | 6/1995 | Clark et al. | 73/865.8 |

FOREIGN PATENT DOCUMENTS

A-4-256842  9/1992  Japan .

*Primary Examiner*—Leo Boudreau
*Assistant Examiner*—Brian P. Werner
*Attorney, Agent, or Firm*—Oliff & Berridge, P.L.C.

[57] ABSTRACT

The present invention provides a method and apparatus for accurately diagnosing a state of damage on a wall of a coking chamber of a coke battery. The method includes accurately diagnosing the damage state of the chamber wall by combination of three detection means. The three detection means include means for photographing the wall of the coking chamber of the coke battery, means for detecting the chamber width between chamber walls by laser range finders, and means for detecting the chamber temperature by radiation thermometers. The joints and the brick surfaces of the coke battery is photographed by a CCD camera. The image of the chamber wall is separated into images of the joints and the brick surfaces. The states of the joints and the brick surfaces are separately recognized to accurately detect damage of the joints and damage of the brick surfaces.

19 Claims, 12 Drawing Sheets

FIG. I

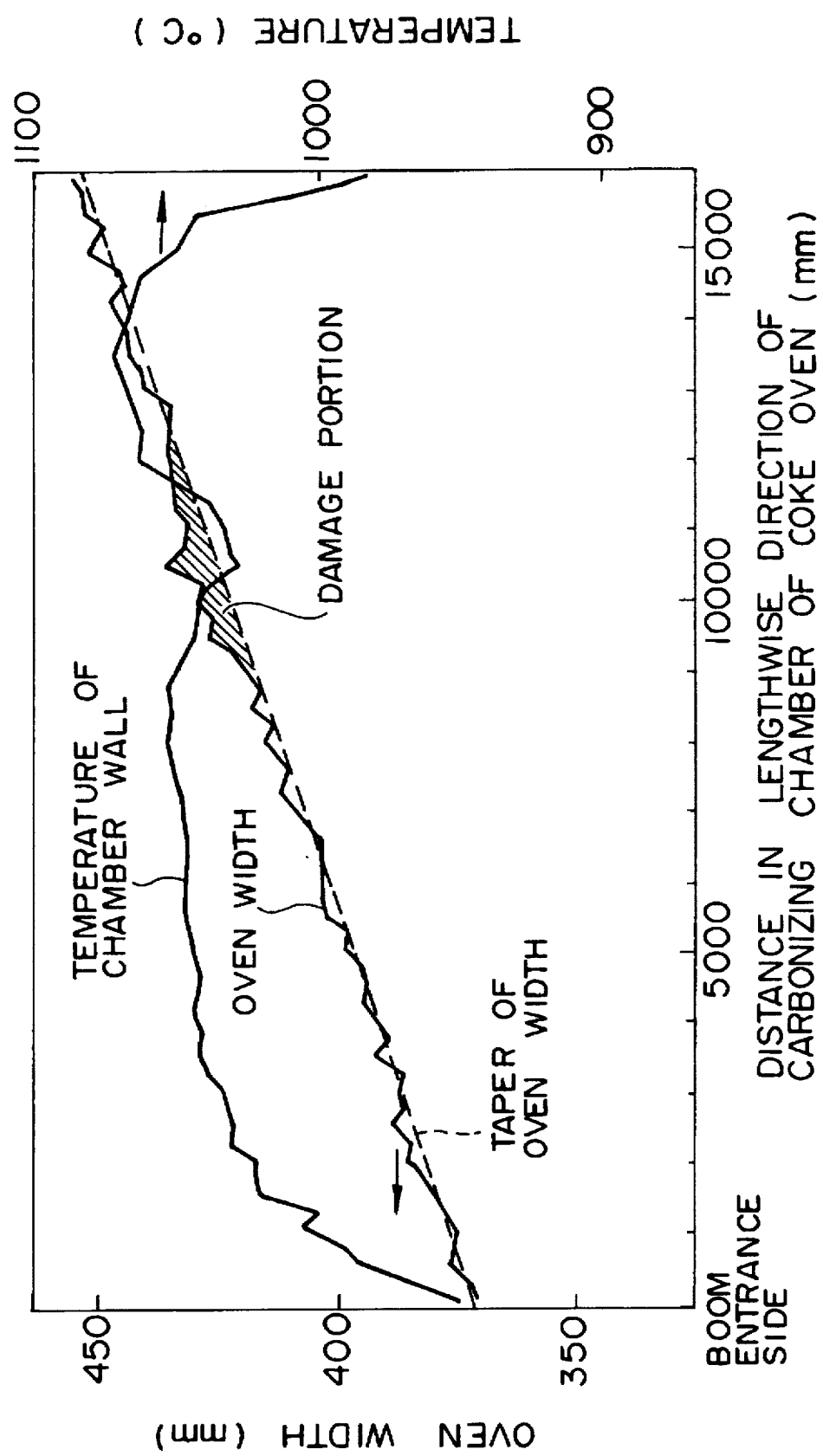

METHOD AND APPARATUS FOR DIAGNOSING WALL OF COKING CHAMBER OF COKE BATTERY

BACKGROUND OF THE INVENTION

1. Field of the Invention

The present invention relates to a method and apparatus for diagnosing the state of a wall of a coking chamber of a coke battery by image processing.

2. Description of the Related Art

Coke is used as a reducing material in operation of a blast furnace and is generally produced by coking coal using a coke battery. A coking chamber of the coke battery is constructed by using fire bricks as a main material because of a high heat load. However, in use for a long time, the chamber wall is sometimes partly damaged by a mechanical external force, thermal stress, the actions of the components of the coal charged, and the like.

In order to maintain the coke battery in a sound state and the operation efficiency at a high level over a long period of time, it is necessary to accurately diagnose the state of a wall of the coking chamber of the coke battery, and repair the wall for increasing the life of bricks by gunning, such as frame gunning, according to demand.

An apparatus comprising a television camera which is inserted into an oven in the lengthwise direction thereof for observing a surface of the chamber wall is known as a chamber wall observation apparatus used for observing the chamber wall. A method of recognizing the state of a wall of the coking chamber of the coke battery from a wall image thereof employs the density value of the whole image. An example of such methods is a method in which, as disclosed in Japanese Patent Laid-Open No. 4-256842, the density value of each of pixels of an image of a chamber wall is compared with a predetermined set value, and pixels within a predetermined range on an image plane comprising a shadow portion and a bright portion are counted. If the count number is larger than a reference value, it is diagnosed that the chamber wall is deteriorating.

However, an image of the chamber wall comprises a joint portion and a brick surface portion, and images of the joint portion and the brick surface have different density distributions. Images of damage of the joint and damage of the brick surface also have different density distributions. The method disclosed in Japanese Patent Laid-Open No. 4-256842 in which the whole image is processed for diagnosing the state of a wall of a coking chamber can be applied to the case where only an image of brick surfaces is displayed on an image plane. However, this method has the problem that it cannot be applied to the case where images of both the joints and the brick surfaces are displayed. The method also has the problem that it is impossible to discriminate states of the chamber wall such as a open brick joint which is damage of a joint, spalling, peeling, etc. which are damage of the brick surfaces, repair marks, deposit carbon, etc.

SUMMARY OF THE INVENTION

The present invention solves the above problems. An object of the present invention is to accurately diagnose the state of a wall of a coking chamber of a coke battery by image processing which permits recognition of the state of a chamber wall, particularly a damage state thereof, even if images of both brick surfaces and joints are displayed on an image plane, and which permits discrimination of states of the chamber wall such as damage of the joints and damage of the brick surfaces, repair marks, deposit carbon, etc., and by employing the chamber width detected by chamber width detection means and/or the chamber temperature detected by chamber temperature detection means.

In order to achieve the object, in accordance with a first aspect of the present invention, there is provided a method of diagnosing a wall of a coking chamber of a coke battery by processing an image of the wall of the coking chamber of the coke battery, comprising separating an image of the chamber wall comprising joints and brick surfaces into an image of the joints and an image of the brick surfaces, and diagnosing the state of the wall of the coking chamber of the coke battery on the basis of the state of the joints recognized from the image of the joints alone, the state of the brick surfaces recognized from the image of the brick surfaces alone, the chamber width of the coke battery coking chamber detected by chamber width detection means and/or the temperature of the coke battery coking chamber detected by chamber temperature detection means.

The principle of the separation into the joint surfaces and the brick surfaces is as follows. FIG. 13 is a graph showing a density distribution of the whole image of a chamber wall in accordance with prior art. Referring to the density distribution of the whole image, since images of joint portions 48 and brick surfaces 49, as shown in FIG. 12, have different density ranges, it is impossible to recognize the state of each of the joint portions and brick surfaces of the chamber wall, particularly damage thereof, from the density distribution of the whole image.

The technique of the present invention thus employs the method of separating the whole image into a joint portion density region 52 and a brick surface density region 53 by utilizing the fact that the joint portions 48 and the brick surfaces 49 have different density ranges, and then respectively recognizing the states of the portions from the density distributions in these regions.

FIG. 14 is a graph showing a density distribution of each of the joint portions and the brick surfaces after separation. When the density distribution of the image of each of the joint portions and the brick surfaces after separation is shown again, the density distribution can be divided into a normal region 54 and a normal and damage region 55 with a threshold value at the boundary therebetween, as shown in FIG. 14. Although the normal and damage region 55 contains damage, noise, deposit carbon and repair marks, since these portions also have different density ranges, the portions can be separated by using density distributions after separation.

In accordance with a second aspect of the present invention, there is provided an apparatus for diagnosing a wall of a coking chamber of a coke battery, comprising a boom with a length which can photograph the coke battery coking chamber over the whole length thereof, chamber wall imaging means provided at the tip of the boom, chamber width detection means and/or chamber temperature detection means, and a lateral oscillation driving mechanism and/or a vertical movement mechanism which is provided on the chamber wall imaging means.

In accordance with a third aspect of the present invention, the apparatus for diagnosing a wall of a coking chamber of a coke battery according to the second aspect further comprises traveling support means provided on the boom, for supporting the boom by slidable contact with the chamber bottom when inserting the boom into the coking chamber of the coke battery.

In accordance with a fourth aspect of the present invention, in the apparatus for diagnosing a wall of a coking chamber of a coke battery according to the second aspect, the boom with a length which permits photography of the coking chamber of the coke battery over the whole length thereof has a water-cooling structure.

In accordance with a fifth aspect of the present invention, in the apparatus for diagnosing a wall of a coking chamber of a coke battery according to the second aspect, the chamber wall imaging means provided at the tip of the boom is provided in a hanger box which is supported in a probe box so as to be laterally oscillatable through a hanger shaft connected to the bottom of the hanger box, and the lateral oscillation driving mechanism, which is connected to the probe box through the hanger shaft, and the chamber width detection means and/or the chamber temperature detection means are provided in a containing box which is integrally connected to the bottom of the probe box.

In accordance with a sixth aspect of the present invention, in the apparatus for diagnosing a wall of a coking chamber of a coke battery according to the fifth aspect, the chamber width detection means and/or the chamber temperature detection means are provided in the probe box in place of provision in the containing box.

In accordance with a seventh aspect of the present invention, in the apparatus for diagnosing a wall of a coking chamber of a coke battery according to the fifth or sixth aspect, the probe box and the containing box has a water-cooling structure.

In the present invention, an image of the chamber wall comprising joints and brick surfaces, which is obtained by photographing the chamber wall, is separated into an image of the joints and an image of the brick surfaces, so that a state of the joints is recognized from the image of the joins alone, and a state of the brick surfaces is recognized from the image of the brick surfaces alone. It is thus possible to recognize the state of the chamber wall even if images of the brick surfaces and the joints having different density distributions are displayed on an image plane. In addition, since the state of the wall of the coking chamber of the coke battery is diagnosed on the basis of the detected chamber width and/or chamber temperature, the state of the chamber wall can securely be diagnosed.

BRIEF DESCRIPTION OF THE DRAWINGS

The invention will be described in detail with reference to the following drawings, wherein like numerals represent like elements and:

FIG. 15 is a drawing showing variations in the chamber width and variations in the chamber temperature in the lengthwise direction of a coking chamber of a coke battery.

DESCRIPTION OF THE PREFERRED EMBODIMENTS

Embodiments of the present invention are described in detail below with reference to the drawings.

Figure 1:
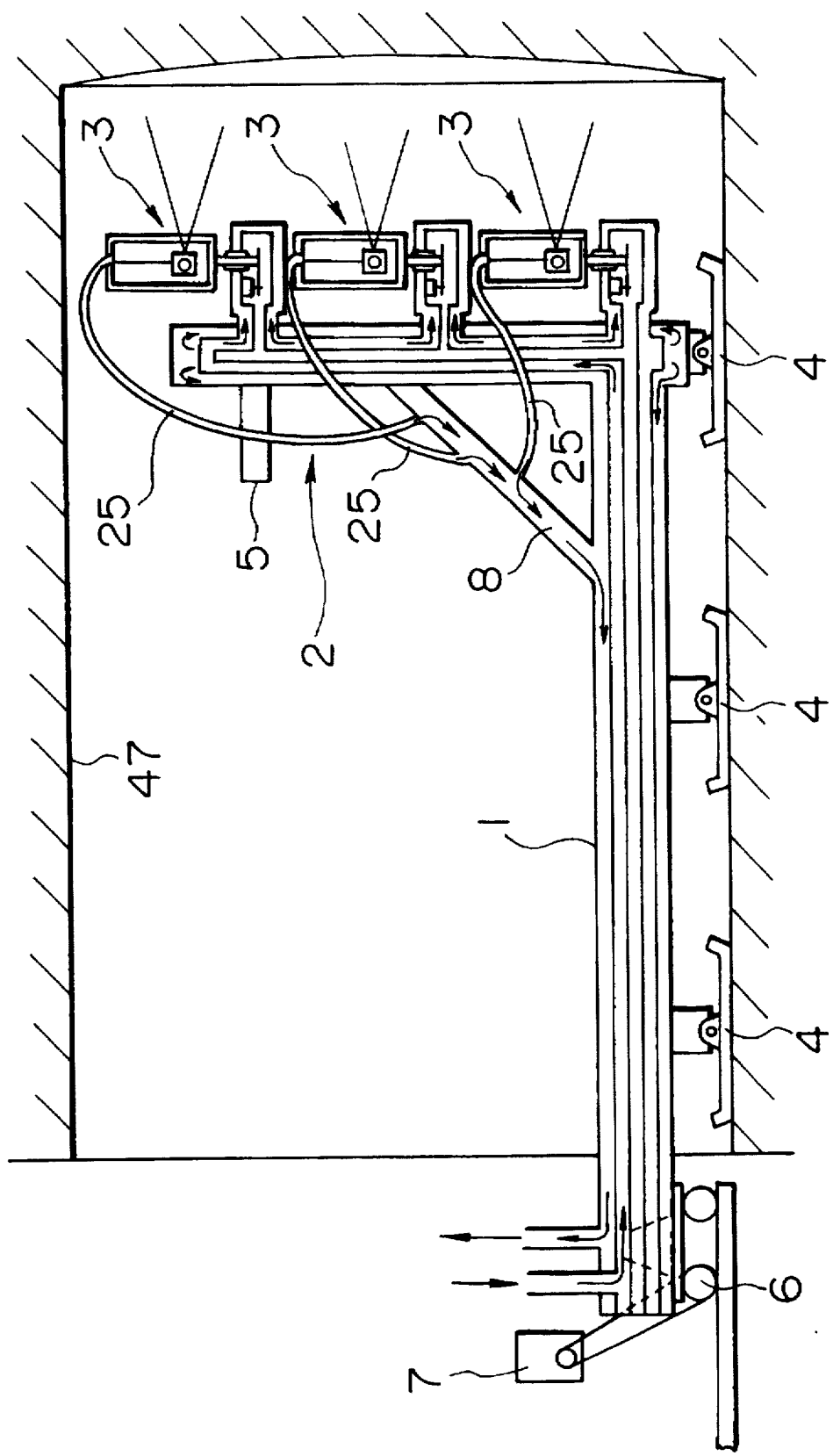
FIG. 1 is a front view illustrating an inner wall observation device inserted into a coking chamber of a coke battery.
Figure 2:
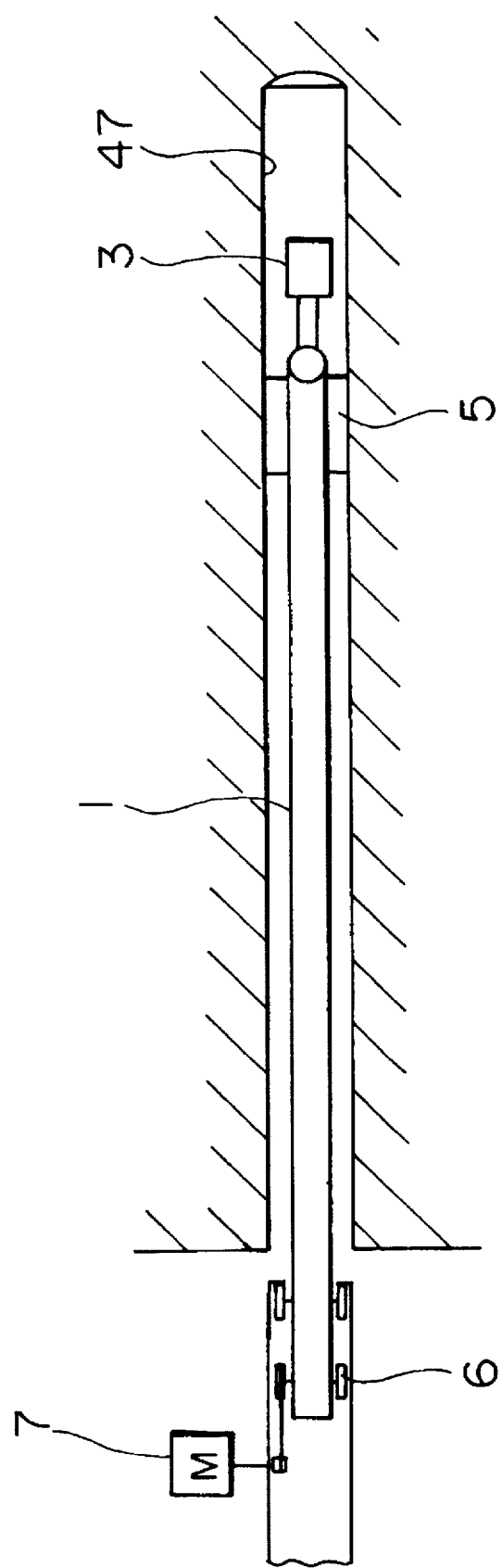
FIG. 2 is a plan view of the inner wall observation device of FIG. 1.
Figure 3:
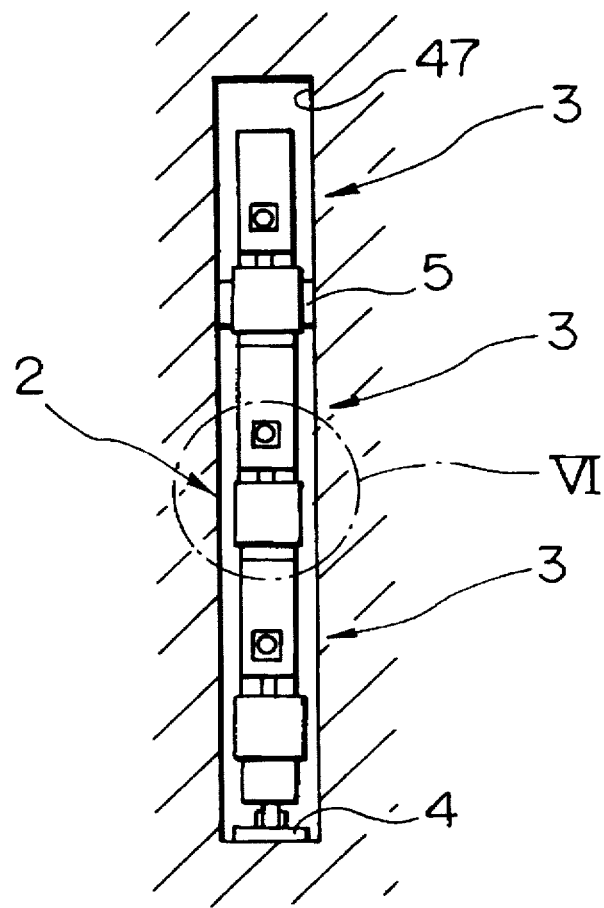
FIG. 3 is a right side view of the inner wall observation device of FIG. 1.

FIG. 1 is a front view showing an inner wall observation device in accordance with an embodiment of the present invention when inserted into a coking chamber of a coke battery; FIG. 2 is a plan view of the inner wall observation device shown in FIG. 1; and FIG. 3 is a right side view of the inner wall observation device shown in FIG. 1.

The inner wall observation device for the coking chamber of the coke battery of this embodiment comprises an insertion boom 1 with a length which permits photographing of the coking chamber of the coke battery of about 16 m long, a vertical boom 2 vertically provided at the tip of the insertion boom 1, and a plurality of probe boxes 3 (in the drawing, three boxes) provided on the vertical boom 2.

Three slide shoes 4 are provided below the insertion boom 1 so as to support the insertion boom 1 by slidable contact with the chamber bottom of the coking chamber of the coke battery. Each of the slide shoes 4 has the form of a sledge made of a steel plate and having a length of about 1500 mm, a base end which is movably supported by the insertion boom 1, and a bottom in contact with the chamber bottom, front and rear ends thereof being greatly rounded in the form of a ski plate in order to decrease sliding resistance at the time of insertion and prevent damage of the chamber bottom.

The these slide shoes 4 enables elongation of the insertion boom 1 without increasing the strength of the insertion boom 1. Side guide shoes 5 of about 1500 mm long are also provided on the right and left sides of the vertical boom 2 substantially at the tip thereof in order to prevent the vertical boom 2 from falling onto the right and left chamber walls during movement.

In FIGS. 1 and 2, reference numeral 7 denotes a motor for driving a wheel 6 provided at the base end of the insertion boom 1 so that the inner wall observation device can be moved in and out of the coking chamber of the coke battery by operating the motor 7.

Figure 4:
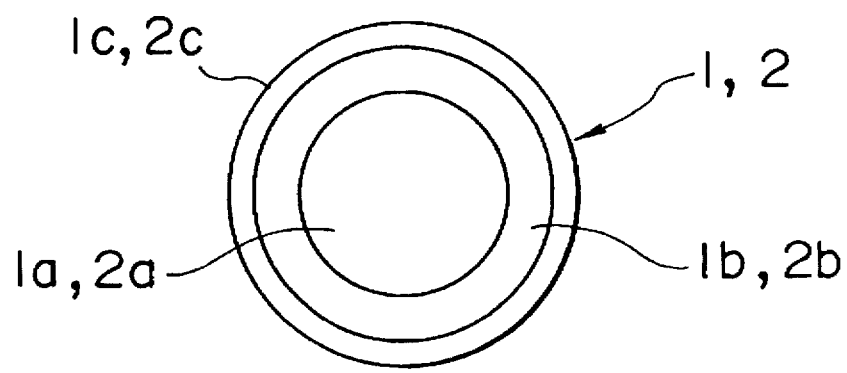
FIG. 4 is a sectional view showing an insertion boom and a vertical boom.

Each of the insertion boom 1 and the vertical boom 2 has a triple pipe structure comprising a central pipe line $1a$ or $2a$ for $N_2$ gas and a wiring cable, an intermediate passage $1b$ or $2b$ for supplying cooling water, and the outermost passage $1c$ or $2c$ for exhausting the cooling water, as shown in a sectional view of FIG. 4. In FIG. 1, reference numeral 8 denotes a inclined drainpipe for connecting the vertical boom 2 and the insertion boom 1 and draining waste water from each of the probe boxes 3.

Figure 5:
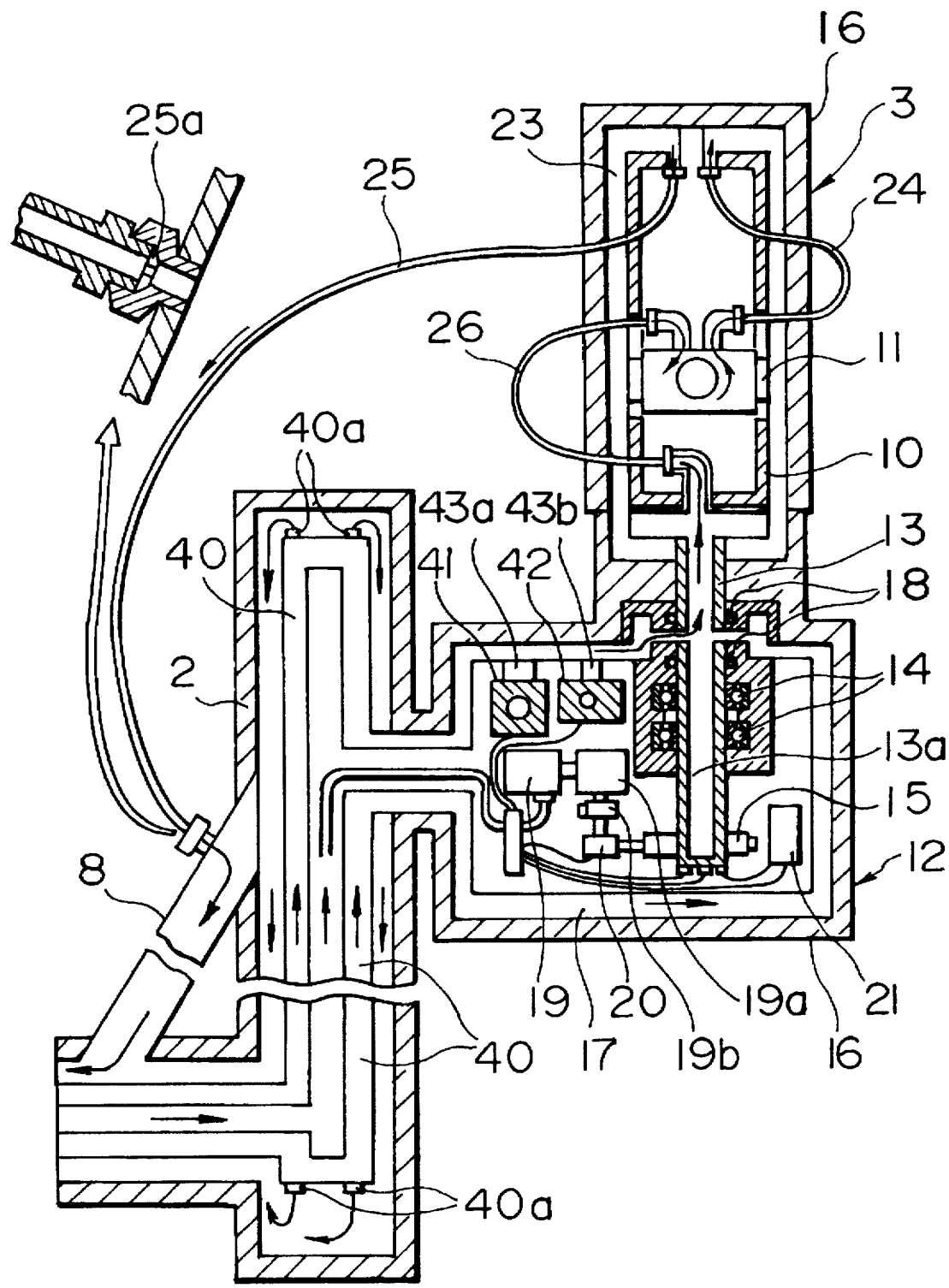
FIG. 5 is a sectional view showing details of a probe box.

FIG. 5 is a sectional view illustrating details of each of the probe boxes 3. Each of the probe boxes 3 comprises a hanger box 10 containing a camera containing case 11, and a camera oscillation driving device containing box 12 having an end which is connected to the vertical boom 2, and the other end at which the camera containing case 11 is rotatably supported.

A hanger shaft 13 which serves as a rotation shaft and which contains a cooling water supply passage 13a is integrally fixed to the base end of the hanger box 10 in which the camera containing case 11 is provided. The hanger shaft 13 is supported by upper and lower bearings 14, which are contained in the camera oscillation driving device containing box 12, and the hanger shaft 13 is connected to a toothed pulley 15. The outer peripheral surface of the probe box 3 is completely covered with ceramic wool 16 having a thermal insulation temperature of 1400° C., the ceramic wool 16 being fixed by covering the whole outer periphery by SUS net which is not shown in the drawings. This cuts off the radiation of heat from the outer periphery of the probe boxes 3 and thus improves the cooling effect of cooling water.

A double outer cooling passage 17 is formed along the outer periphery of the camera oscillating driving device containing box 12 so as to be connected to the cooling water supply passage 2b of the vertical boom 2, and further connected to a cooling water supply passage 13a of the hanger shaft 13.

Reference numeral 18 denotes O rings provided on the hanger shaft 13, for preventing leakage of water. Reference numeral 19 denotes a geared motor comprising a toothed pulley 19b provided on the output shaft thereof through a speed reducer 19a, a toothed pulley 15 being connected to the toothed pulley 19b so as to rotate the hanger shaft 13. A pulse generator 20 is disposed on an extension of the output shaft of the geared motor 13 so as to feed back rotation of the hanger shaft 19.

The foregoing structure permits rotation of the camera containing case 11 around the hanger shaft 13. In a conventional apparatus, a camera is rotated within a box, and is thus rotated within only a narrow range in an observation window. However, in the present invention, because the camera is rotatably disposed outside the box, a wide range of viewing field can be obtained, and no damage state of the chamber wall is overlooked during imaging, thereby securely obtaining information necessary for a repair work.

Figure 6:
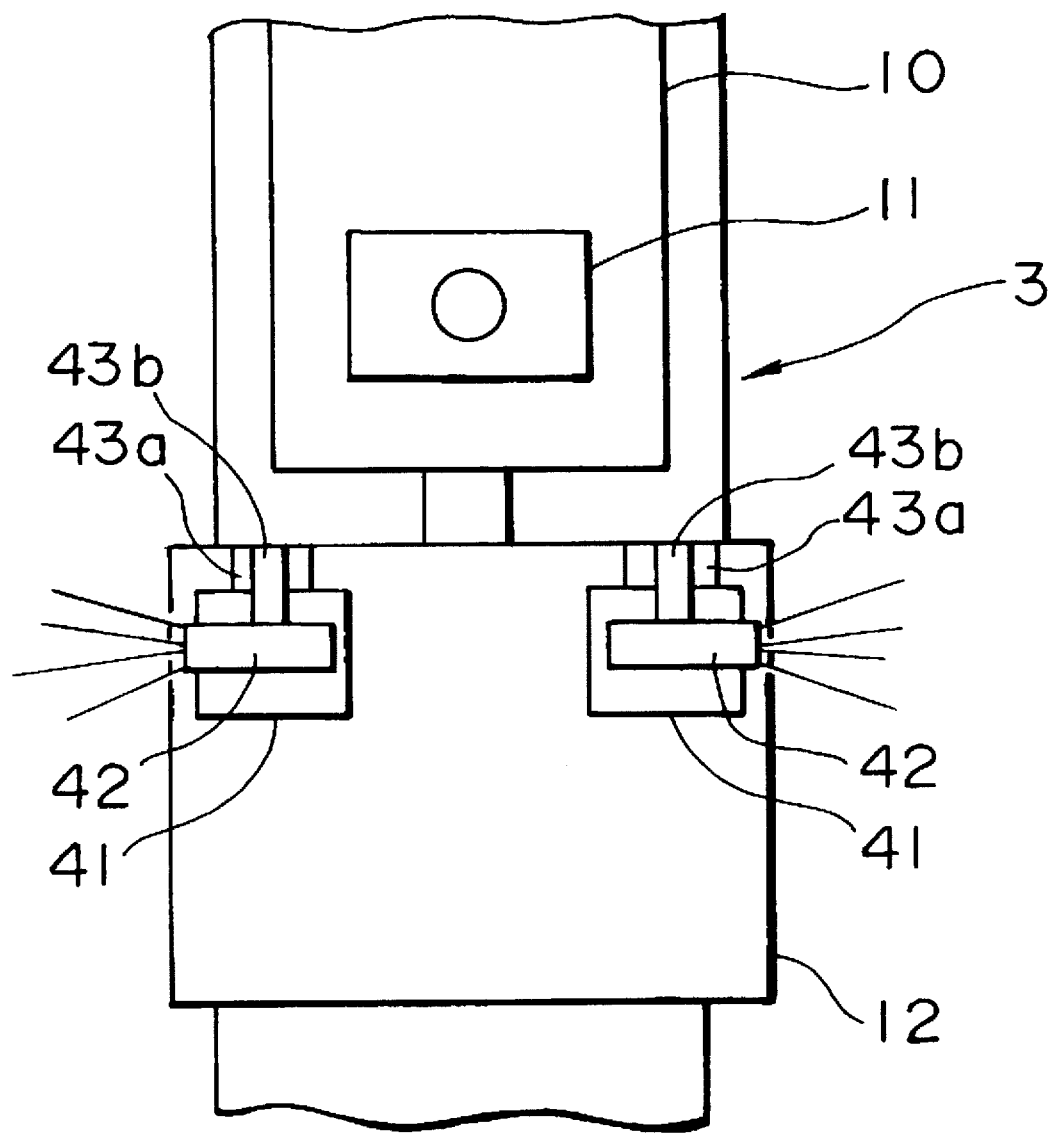
FIG. 6 is a partially enlarged view showing the portion V1 shown in FIG. 3.

A controller 21 of a CCD (Charge Coupled Device) camera which will be described below is also disposed in the camera oscillation driving device containing box 12, and all cables are collected in the camera oscillation driving device containing box 12, passed through the $N_2$ gas and wiring cable pipe lines 1 and 2a of the insertion boom 1 and the vertical boom 2 and connected to an outer signal processor 44. In the camera oscillation driving device containing box 12 are symmetrically provided right and left laser range finders 41 and radiation thermometers 42 through brackets 43a and 43b, respectively, as shown in FIGS. 5 and 6. The laser range finders 41 and the radiation thermometers 42 are disposed at right angles with the side walls of a coking chamber 47 of the coke battery in the lengthwise direction thereof so that laser beams are respectively applied to the lengthwise side walls from the right and left laser range finders 41 to determine the distance between the both side wall surfaces by receiving the reflected laser beams, and the temperatures of the both side walls are respectively measured by the radiation thermometers 42.

Similarly, a cooling passage 23 is formed along the outer periphery of the hanger box 10 containing the camera containing box 11, the cooling passage 23 having an inlet side which is connected to a flexible hose 24 connected to the camera containing case 11, and an outlet side which is connected to a flexible hose 25 connected to the inclined drainpipe 8. The cooling water supply passage 13a of the hanger shaft 13 is connected to the camera containing box 11 by a flexible hose 26. In the flexible hose 26 are passed a laser range finder cable, a radiation thermometer cable, a signal cable of CCD camera 32, an auto-iris cable, a $N_2$ purge cable, etc. so that a camera image can be received, and the chamber width and chamber temperature can be measured. Since cooling water is of course passed through the flexible hose, the inlet and outlet of each of the cables are completely sealed by rubber bushing.

Figure 7:
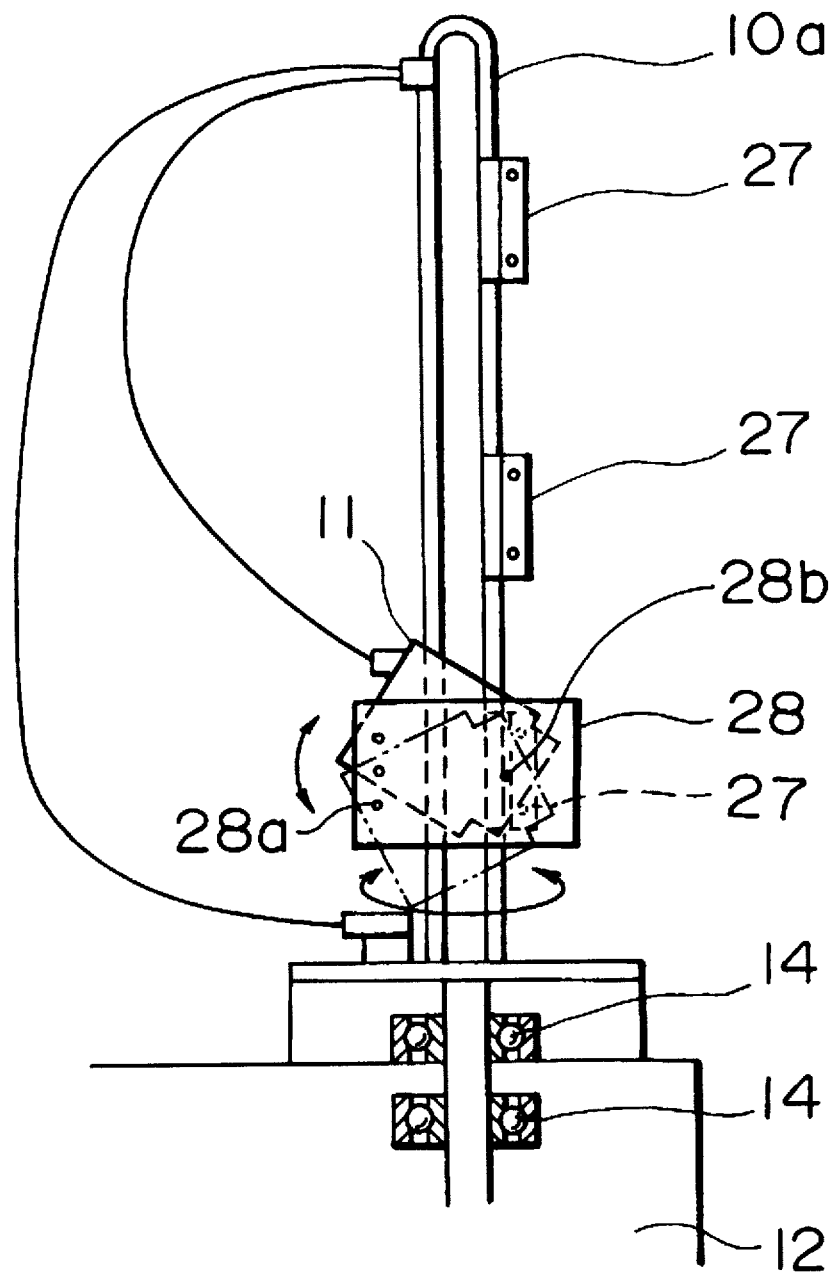
FIG. 7 is a drawing showing details of a hanger portion.

FIG. 7 is a drawing showing details of a hanger 10a for fixing the camera containing case 11, the hanger 10a comprising a plurality of mounting brackets 27, and a fixing bracket 28 provided on one of the mounting brackets 27 and having a plurality of mounting holes 28a so that the fixing bracket 28 can be vertically tilted with a vertical rotational pin 28b as a shaft. The camera containing case 11 is fixed to the fixing bracket 28. This structure permits the camera containing case 11 mounted on the hanger 10a to be not only horizontally rotated around the hanger shaft 13 as a rotational shaft, but also fixed at any desired vertical position and vertically tilted. It is thus possible to photograph a portion out of the field of view of the camera by changing the mounting position. It is also possible to photograph the top wall surface by directing upward the uppermost CCD camera 32.

Figure 8:
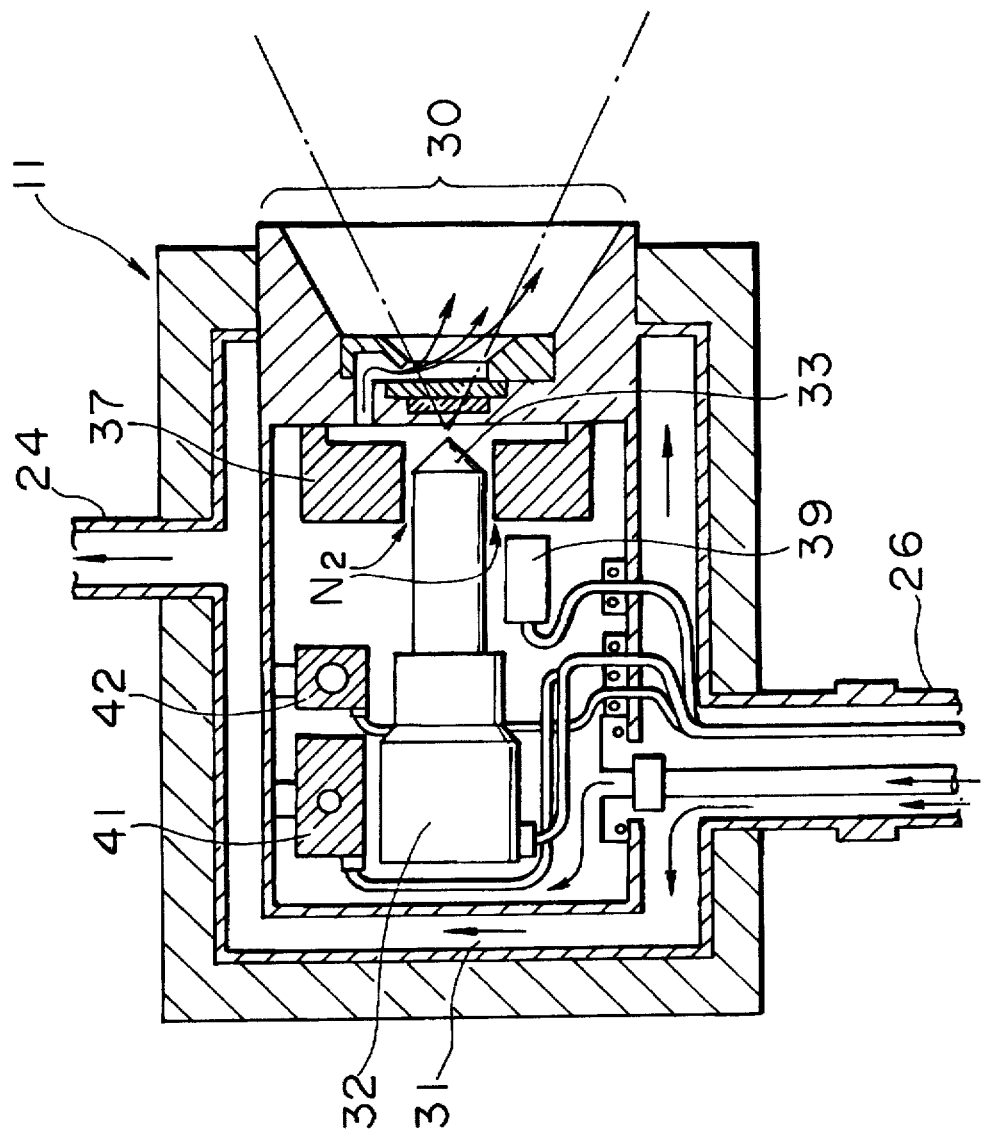
FIG. 8 is a sectional view showing details of a camera containing case.
Figure 9:
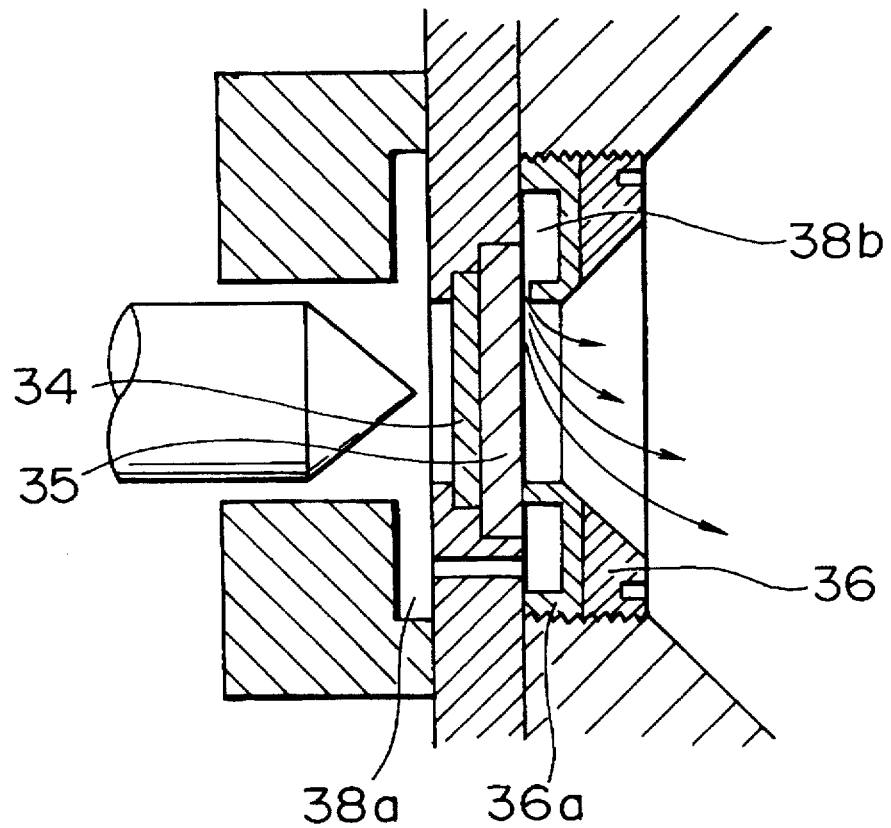
FIG. 9 is a partially enlarged view showing a window of a camera containing case.
Figure 10:
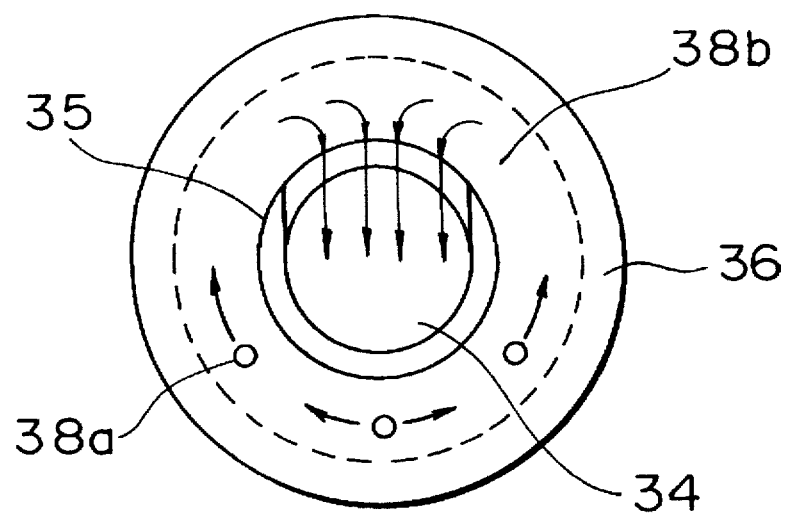
FIG. 10 is a front view showing a window of a camera containing case.

FIG. 8 is a drawing showing details of the camera containing case 11, FIG. 9 is a partially enlarged view of a window of the camera containing case 11, and FIG. 10 is a front view of the same window. One side of the camera containing case 11 is open to form an observation window 30, and an outer cooling passage 31 is formed along the outer periphery of the camera containing case 11. The CCD camera 32 and a pinhole lens 33 of about diameter 3 mm are provided in the camera containing case 11, and filter glass 34 and heat resistance glass 35 are disposed in front of the pinhole lens 33, the filter glass 34 and heat resistance glass 35 being fixed by a metallic presser member 36. The metallic presser member 36 has a screwing structure and enables the heat resistance glass 35 to be detachable from the outside. The filter glass 34 is effective for controlling unnecessary wavelength input due to halation, temperature, and the like when the data obtained by the CCD camera 32 is displayed on a monitor. The metallic presser member 36 is adapted for pressing the whole periphery by the screwing structure, and has a structure with a purge slit which enables setting at any desired circumferential position so as to permit downward purging. The structure prevents convection because of a one-direction flow of purge and permits coke powder which adheres to the glass surface to be blown away by purging $N_2$ gas in one direction along the glass surface. The pressing surface between the metallic presser member 36a and the heat resistance glass 35 has a structure having a header groove 38b formed in the whole periphery of the $N_2$ gas passage so that the effect of a temperature rise of the metallic presser member 36a on the heat resistance glass 35 can be minimized.

Reference numeral 37 denotes a guard plate for filling the gap between the window and the pinhole lens 33 so as to cut off radiant heat which leaks and enters from the window, and which is applied to the CCD camera 32. In the camera containing case 11 is provided a sensor 39 for detecting an abnormality when the temperature in the camera rises to 50° C. or more. The sensor 39 is connected to the motor 7 shown in FIG. 1 so that, when the sensor 39 detects an abnormality, it operates the motor 7 to rapidly return the inner wall observation device to the outside of the chamber for protecting the CCD camera 32. Since the CCD camera 32 is provided with an electronic shutter function, clear observation can be carried out without being affected by vibration of the slide shoes 4 during traveling.

The pinhole lens 33 comprises a wide-angle lens having a horizontal covering angle of about 56 degrees, a vertical covering angle of about 43 degrees, a diagonal covering angle of about 69 degrees, and a tip lens diameter of about diameter 3 mm. This pinhole lens 33 can decrease the diameter of the window to about 22 mm, and thus minimize radiant heat from the window. As clearly shown in FIGS. 9 and 10, a $N_2$ gas release groove 38a is provided above the heat resistance glass 35 in order to release $N_2$ gas flowing in the header groove 38b in the downward direction along the heat resistance glass 35. This can prevent the adhesion of dust particles to the surface of the heat resistance glass 35, and cool the heat resistance glass 35.

Since the CCD camera 32 is a separate type camera which is divided into a controller unit and a CCD camera which comprises only a lens unit and a CCD element unit, the camera can be made compact, and the size of the camera containing box 11 can be decreased. The cable of the CCD camera signal line is disposed in the flexible hose 26 for supplying cooling water to cool the camera.

The laser range finders 41 for detecting the distance to a surface of the chamber wall, and the radiation thermometers 42 for detecting the temperature of the surface of the chamber wall may be installed in the camera containing case 11 disposed in the probe box 3, as shown in FIG. 8. In this case, the laser range finders 41 and the radiation thermometers 42 are not installed in the camera oscillation drive containing box 12.

The front side of each of the laser range finders 41 and the radiation thermometers 42 has a structure corresponding to the structure in front of the CD camera 32 using heat resistance glass so as to enable measurement of the side wall surface of the coking chamber of the coke battery.

Each of the above flexible hoses 24, 25 and 26 is wound by SUS (JIS stainless steel) net, and the outer periphery thereof is taped with a heat resistance tape (1400° C.) for protecting these hoses against radiant heat. This provides the water passage with flexibility and is thus effective to smooth the oscillation of the camera hanger. In this embodiment, all box materials comprise SUS material for sufficiently attaining the heat resistance temperature of 50° C. of the CCD camera by using cooling water, heat resistance material and $N_2$ gas. However, the use of a copper material further improves heat conductivity and is thus effective for protecting the camera.

Description will now be made of the flow of cooling water in the inner wall observation device of the coking chamber of the coke battery.

The cooling water supplied to the cooling water supply passage 1b from the base end of the insertion boom 1 is passed through the cooling water supply passage 2b of the vertical boom 2 and supplied to several probe boxes 3. Waste water of the probe boxes 3 is drained from the drain passage 1c of the insertion boom 1 through the flexible hose 25. Many nozzle holes 40a are provided on the upper and lower ends of the header pipe 40 of the vertical boom 2 shown in FIG. 5. Waste water is passed through the drain passage 2c outside the header pipe 40 from the nozzle holes 40a, and caused to flow out to the drain passage 1c of the insertion boom 1.

On the other hand, the cooling water sent into the camera oscillation drive containing box 12 from the header pipe 40 is passed through the double outer cooling passage 17 of the camera oscillation drive containing box 12 for cooling the all surfaces of the camera oscillation drive containing box 12, and then caused to flow into the cooling water supply passage 13a of the hanger shaft 13. At this time, the bearing 14 and the O ring 18 are cooled. The cooling water is then passed through the flexible hose 26 and the double outer cooling passage 31 of the camera containing case 11 to cool the all surfaces of the camera containing case 11. The cooling water is further passed through the flexible hose 24, passed downward through the double outer cooling passage 23 of the hanger box 10, and again returned to the upper portion of the hanger box 10. The cooling water is then passed through the flexible hose 25 from the upper portion and further passed through the inclined drainpipe 8 and the drain passage 1c of the insertion boom 1 to be drained out to the outside.

The amounts of the water supplied to the respective probe boxes 3 from the header pipe 40 can be balanced by providing the outlet of each of the flexible hoses 25 with an orifice as a SUS plate-formed flow resistance material with a hole having an inner diameter smaller than that of the hose in accordance with differences in height. Since the amount of the cooling water supplied to the camera containing case 11 depends upon the heat resistance (50°) of the camera body, the drain passage 2c is controlled by plugging the nozzle holes 40a provided at the upper and lower ends of the header pipe 40 every multiple of 4 seconds, thereby securing the flow rate of each of the probe boxes 3.

Figure 11:
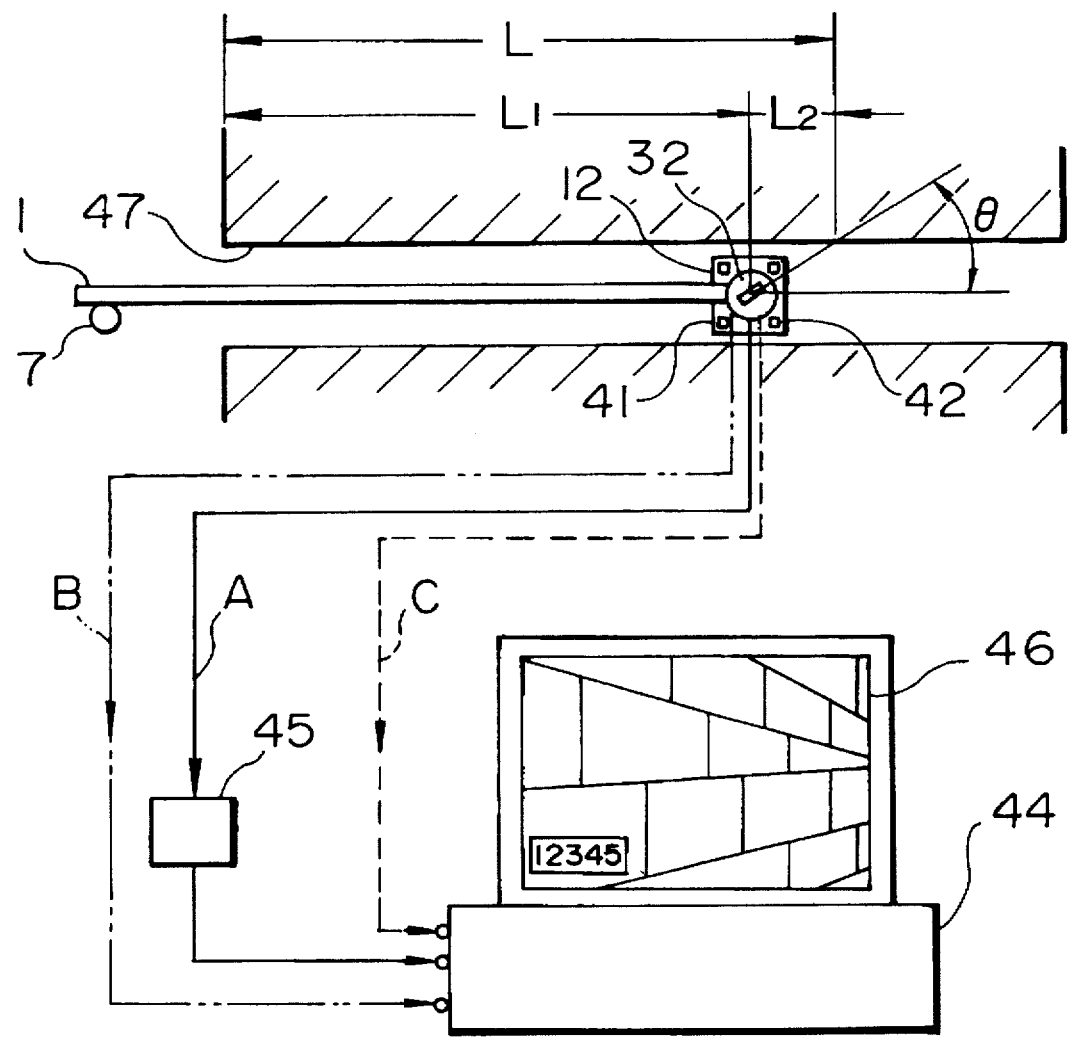
FIG. 11 is a drawing showing the whole system of an inner wall observation device of a coking chamber of a coke battery.

FIG. 11 is a drawing showing the entire system of the inner wall observation device for the coking chamber of the coke battery. Reference numeral 45 denotes a high-speed counter connected to a pulse generator of the driving motor 7 and a pulse generator 20 provided in the camera oscillation drive containing box 12, reference numeral 44 denotes a signal processor for converting the numerical value obtained by the high-speed counter into video output, and reference numeral 46 denotes a television monitor for the video output. As data for the television monitor 46 to display, record and analyze the image taken by the CCD camera 32, an amount of movement of the insertion boom 1 on an extension of the driving shaft thereof is detected by the pulse generator of the motor 7, and the angle of oscillation of the camera at the tip of the boom is detected by the pulse generator 20. The input from both pulse generators is computed, and the position of a center mark displayed on the television monitor 46 can thus be displayed as the distance to the inlet of the chamber at the four corners of the television monitor 46. The possibility of determining the distance of the center mark displayed is effective for means for analyzing data obtained by visual observation of the state of a chamber wall and processing an image.

Figure 12:
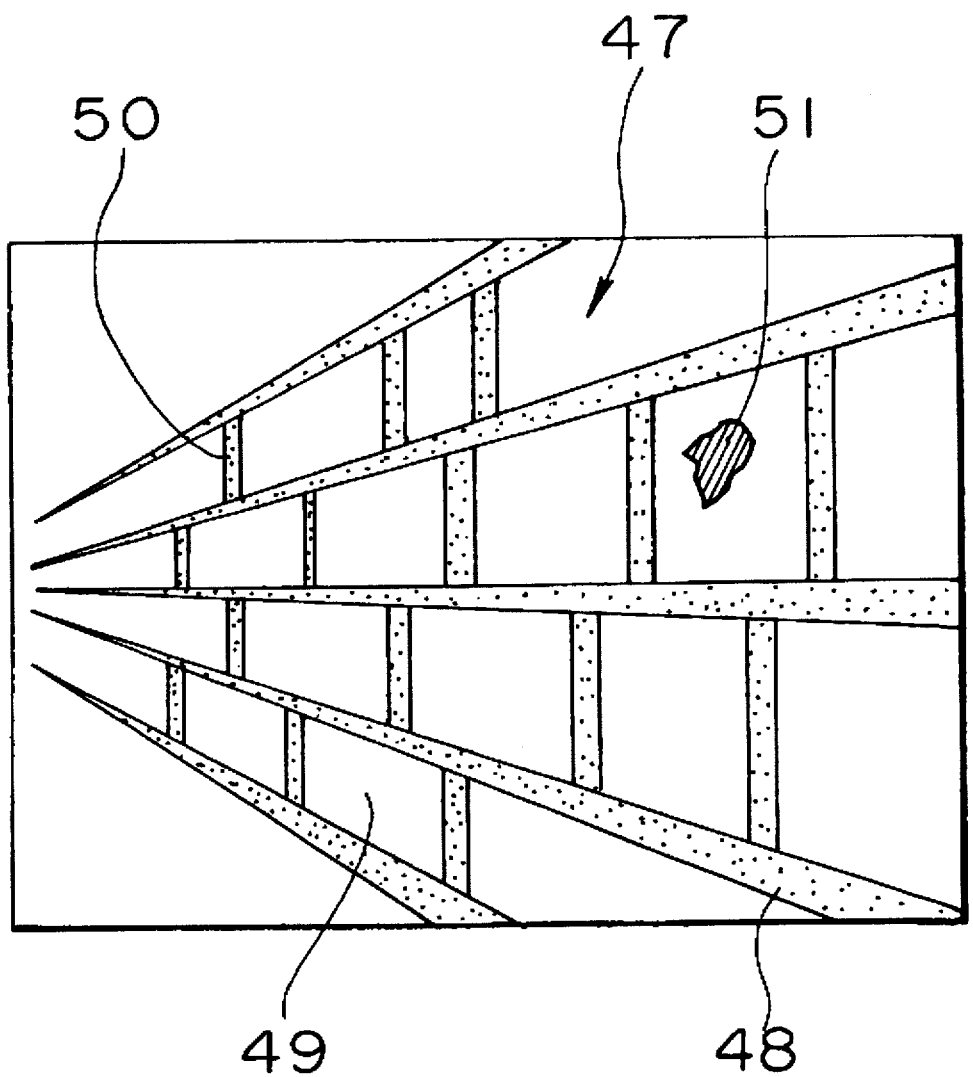
FIG. 12 is a drawing illustrating an image of a chamber wall.
Figure 13:
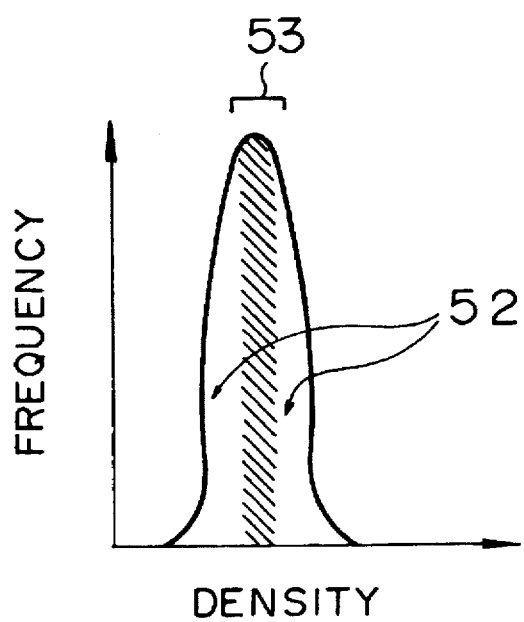
FIG. 13 is a graph showing a density distribution of the whole image of a chamber wall.

When the state of a wall of the coking chamber 47 of the coke battery is diagnosed by image processing, the insertion boom 1 is inserted into the coking chamber 47, and the chamber wall is photographed by using the CCD camera 32 disposed in the lengthwise direction of the vertical boom 2. Photographic signal A is input to the signal processor 44 through the controller 21. The angle of the CCD camera 32 is previously adjusted for photographing a surface of the chamber wall so that the surface of the chamber wall is photographed at equal intervals during the movement of the insertion boom 1 at a constant speed. The state of the chamber wall is recognized by the signal processor 44 based on the photographic image. FIG. 12 shows the image of the chamber wall photographed, which comprises joint portions 48 and brick surfaces 49, damage of the joint portions including a open brick joint 50, and damage of the brick surfaces including spalling separation 51 and the like. Other examples of states of the chamber wall include repair marks which occur in repair of damage, deposit carbon, etc. which are observed on the brick surfaces. FIG. 13 is a graph showing a density distribution of the whole image of the chamber wall. Referring to the density distributing of the whole image, the states of the joint portions 48 and the brick surfaces 49 of the chamber wall, particularly damage thereof, cannot be recognized because images of the joint portions 48 and the brick surfaces 49 have different density ranges, as shown in FIG. 13.

Therefore, a method is employed in which the density distribution is separated into a joint portion density region 52 and a brick surface density region 53 based on the fact that image of the joint portions 48 and the brick surfaces 49 have different density ranges, and the states of the joint portions 48 and the brick surfaces 49 are recognized from the density distributions in the two regions. However, since, in this embodiment, an image is subjected to significant shading with a difference in brightness between a front portion and a rear portion, shading correction, smoothing and binary processing are performed as preprocessing for separation.

Figure 14:
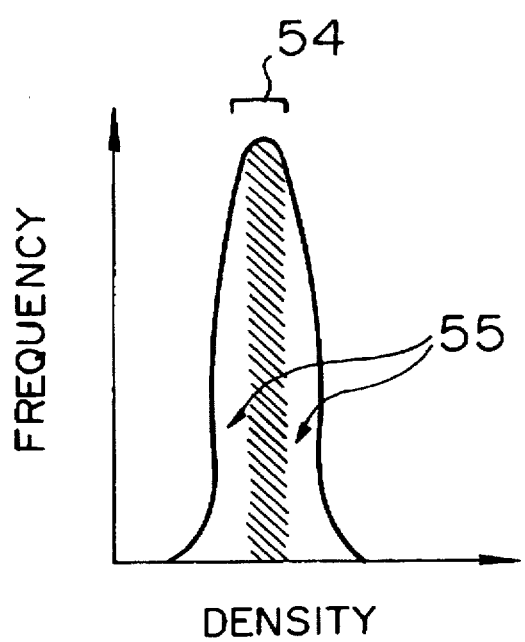
FIG. 14 is a graph showing a density distribution of each of joint portions and brick surfaces after separation.

FIG. 14 is a graph showing a density distribution of each of the joint portions and the brick surfaces after separation. When, after separation, the density distributions of images of the joint portions and the brick surfaces are separately shown, each of the density distributions can be divided into a normal region 54 and a normal and damage region 55 with a threshold value at the boundary therebetween, as shown in FIG. 14. Although the normal and damage region 55 contains noise, deposit carbon and repair marks other than damage, since these regions have different density ranges, the regions can be separated by using density distributions after separation. In this embodiment, each of the thresholds value used for separating into damage and so on using the density distributions is computed from an average density and a density distribution value.

In the present invention, a surface of the chamber wall is photographed by using the CCD camera 32 in the above-described manner, and the image obtained is separated into the joint portion density region 52 and the brick surface density region 53, as shown in FIG. 13. The damage portion is recognized by the density distribution of each of the regions, as shown in FIG. 14, and the damage portion of the chamber wall is more accurately recognized by using the laser range finders 41 and the radiation thermometers 42 which are disposed in the camera oscillation drive containing box 12.

Namely, signal B of the distance to the surface of the chamber wall is measured by using the left and right range finders 41 disposed in the camera oscillation drive containing box 12 during the movement in the oven along the lengthwise direction of the chamber wall, as shown in FIG. 11, and is transmitted to the signal processor 44 through the controller 21 (refer to FIG. 5). The signal B is recorded as the width of the coking chamber in the signal processor 44. Signal C of the temperature of the surface of the chamber wall measured by the left and right radiation thermometers 42 is also transmitted to the signal processor 44 through the controller 21, and recorded as the temperature of the coking chamber 47 in the signal processor 44.

FIG. 15 shows variations in the chamber width (mm) which is measured by the laser range finders 41 and based on the taper of the oven width, which is shown by a dotted line, and variations in the temperature (° C.) of the chamber wall detected by the radiation thermometers 42 in the lengthwise direction of the coking chamber of the coke battery. The position on the brick surfaces which is recognized as a damage portion by photographing by the CCD camera 32 coincided with the position detected as a portion where the oven width is significantly increased on the basis of the taper of the oven width, as shown in FIG. 15. In this damage portion, the temperature detected by the radiation thermometers 42 is lower than the temperatures of other portions. It was thus found that the damage portions detected by the three detection means completely coincide.

When damage of the wall of the coking chamber of the coke battery is diagnosed by using only the CCD camera 32, the damage is judged on the basis of the area alone. However, in the present invention, the measurement of the chamber width using the laser range finders 41 permits not only judgement of the depth of damage but also measurement of expansion of the whole oven body. Since a required amount of repair can be quantified based on the detected position, area and depth of damage, a plan can be made to repair the wall of the coking chamber of the coke battery. Since the temperature distribution of the chamber wall detected by the radiation thermometers 42, it is possible to more accurately judge the damage portion of the coking chamber wall. The present invention enables the judgement of an abnormality of the chamber wall, which cannot be judged by image processing alone, and can thus improve the rate of recognition of the damage portion.

In some cases, the present invention enables combination of the CCD camera 32 and the laser range finders 41, or combination of the CCD camera 32 and the radiation thermometers 42. The measurement means used is not limited to the CCD camera 32, the laser range finders 41, the radiation thermometers 42, and other means corresponding to these measurement means can also be used.

As described above, the present invention has the excellent effects that, even if the brick surfaces and the joints having different density distributions are displayed on an image plane, the state of the chamber wall can be accurately recognized by separating these portions, and that states of the chamber wall such as damage of the joints and damage, repair marks and carbon adhesion of the brick surfaces can further be discriminated. Since a damage portion of the chamber wall is judged on the basis of the chamber width detected by the chamber width detection means and/or the chamber temperature detected by the chamber temperature detection means, the state of the wall of the coking chamber of the coke battery can reliably be diagnosed.

Further, the present invention permits quantitative determination of not only a damage state of the chamber wall but also distortion of the oven body, and the temperature distribution of each of coking chambers, thereby enabling the practice of a systematic repair of the chamber wall.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A method for diagnosing a state of a wall of a coke battery coking chamber, the method comprising:

forming an image of the wall with chamber wall imaging means, a camera portion of the chamber wall imaging means being disposed at a tip of the boom, the boom being inserted into the coke battery coking chamber so that the camera portion of the chamber wall imaging means is moved along a length of the coke battery coking chamber to form the image of the wall;

separating the image into a joint image and a brick surface image based on a density distribution difference between the joint image and the brick surface image; and diagnosing the state of the wall by separately analyzing the joint image and the brick surface image.

2. The method of claim 1, further comprising:

detecting a width of the coke battery coking chamber along the length of the coke battery coking chamber, the width being detected by chamber width detection means; and diagnosing the state of the wall based on the width of the coke battery coking chamber.

3. The method of claim 1, further comprising:

detecting a chamber temperature of the coke battery coking chamber along the length of the coke battery coking chamber, the chamber temperature being detected by chamber temperature detection means; and diagnosing the state of the wall based on the chamber temperature of the coke battery coking chamber.

4. The method of claim 1, wherein the diagnosing step comprises:

diagnosing a state of a joint portion of the wall by analyzing a joint image density; and diagnosing a state of a brick surface portion of the wall by analyzing a brick surface image density.

5. An apparatus that diagnoses a state of a wall of a coke battery coking chamber, comprising:

a boom; and chamber wall imaging means for forming an image of the wall, a camera portion of the chamber wall image means being disposed at a tip of the boom, the boom being inserted into the coke battery coking chamber so that the chamber wall imaging means is moved along a length of the coke battery coking chamber to form the image of the wall, wherein the chamber wall imaging means separates the image into a joint image and a brick surface image based on a density distribution difference between the joint image and the brick surface image, and diagnoses the state of the wall by separately diagnosing the joint image and the brick surface image.

6. The apparatus of claim 5, further comprising:

chamber width detection means coupled to the chamber wall imaging means for detecting a width of the coke battery coking chamber along the length of the coke battery coking chamber, wherein the chamber wall imaging means diagnoses the state of the wall based on the width of the coke battery coking chamber.

7. The apparatus of claim 5, further comprising:

chamber temperature detection means coupled to the chamber wall imaging means for detecting a chamber temperature of the coke battery coking chamber along the length of the coke battery coking chamber, wherein the chamber wall imaging means diagnoses the state of the wall based on the chamber temperature of the coke battery coking chamber.

8. The apparatus of claim 5, further comprising:

a lateral oscillation drive mechanism connected to the chamber wall imaging means, the lateral oscillation drive mechanism rotating the camera portion of the chamber wall imaging means in a plurality of lateral directions for forming the image of the wall.

9. The apparatus of claim 5, further comprising:

a vertical movement mechanism connected to the chamber wall imaging means, the vertical movement mechanism rotating the chamber wall imaging means in a plurality of vertical directions for forming the image of the wall.

10. The apparatus of claim 5, further comprising:

a traveling support device connected to the boom for supporting the boom, the traveling support device being in slidable contact with a chamber bottom of the coke battery coking chamber when the boom is inserted into the coke battery coking chamber.

11. The apparatus of claim 5, wherein the boom comprises:

first water-cooling means for cooling the boom and transporting cooling water.

12. The apparatus of claim 5, further comprising:

a hanger box disposed at the tip of the boom containing the camera portion of the chamber wall imaging means;

a hanger shaft connected to the hanger box;

a probe box supporting the hanger shaft so that the hanger shaft and the hanger box can oscillate;

a containing box connected to a bottom of the probe box; and a lateral oscillation drive mechanism connected to the hanger shaft, the lateral oscillation drive mechanism oscillating the hanger shaft and the hanger box, wherein the camera portion of the chamber wall imaging means is rotated in a plurality of lateral directions for forming the image of the wall of the coke battery coking chamber.

13. The apparatus of claim 12, further comprising:

chamber width detection means disposed in the containing box for detecting a width of the coke battery coking chamber, wherein the chamber wall imaging means diagnoses the state of the wall based on the width of the coke battery coking chamber.

14. The apparatus of claim 12, further comprising:

chamber temperature detection means disposed in the containing box for detecting a chamber temperature of the coke battery coking chamber, wherein the chamber wall imaging means diagnoses the state of the wall based on the chamber temperature of the coke battery coking chamber.

15. The apparatus of claim 12, further comprising:

chamber width detection means disposed in the probe box for detecting a width of the coke battery coking chamber, wherein the chamber wall imaging means diagnoses the state of the wall based on the width of the coke battery coking chamber.

16. The apparatus of claim 12, further comprising:

chamber temperature detection means disposed in the probe box for detecting a chamber temperature of the coke battery coking chamber, wherein the chamber wall imaging means diagnoses the state of the wall based on the chamber temperature of the coke battery coking chamber.

17. The apparatus of claim 12, wherein the probe box comprises:

second water-cooling means for cooling the probe box and transporting cooling water.

18. The apparatus of claim 12, wherein the containing box, comprises:

third water-cooling means for cooling the containing box and transporting cooling water.

19. The apparatus of claim 5, wherein the chamber wall imaging means diagnoses the state of the wall by analyzing a joint image density and a brick surface image density separately formed for a joint portion and a brick surface portion of the wall, respectively.

* * * * *

UNITED STATES PATENT AND TRADEMARK OFFICE
CERTIFICATE OF CORRECTION

PATENT NO. : 5,715,328
DATED      : February 3, 1998
INVENTOR(S): Yuji TSUKIHARA It is certified that error appears in the above-indentified patent and that said Letters Patent is hereby corrected as shown below:

On the title page, item [73]:

In the Assignment, change the Assignee from "Kawasaki Steel Techno-Research Corporation" to --Kawasaki Steel Corporation--.

Signed and Sealed this

Seventh Day of July, 1998

Attest:

BRUCE LEHMAN

*Attesting Officer*     *Commissioner of Patents and Trademarks*